United States Patent [19]

Roll

[11] Patent Number: 5,419,764
[45] Date of Patent: May 30, 1995

[54] PERCUTANEOUS TWISTING LOCK CATHETER

[76] Inventor: John D. Roll, 5953 Shelford La., Rockford, Ill. 61107

[21] Appl. No.: 183,338

[22] Filed: Jan. 19, 1994

[51] Int. Cl.$^6$ .................................................. A61M 5/32
[52] U.S. Cl. ..................................... 604/95; 604/174; 604/178; 604/280
[58] Field of Search ................. 604/27, 51, 95, 93, 604/264, 280, 34, 242, 249, 281, 174, 178

[56] References Cited

U.S. PATENT DOCUMENTS

| | | | |
|---|---|---|---|
| 4,586,923 | 5/1986 | Gould et al. | 604/95 |
| 4,643,720 | 2/1987 | Lanciano . | |
| 4,664,113 | 5/1987 | Frisbie et al. | 604/96 |
| 4,740,195 | 4/1988 | Lanciano . | |
| 5,030,204 | 7/1991 | Badger et al. . | |
| 5,041,085 | 8/1991 | Osborne et al. . | |
| 5,185,004 | 2/1993 | Lashinski | 604/280 |

*Primary Examiner*—C. Fred Rosenbaum
*Assistant Examiner*—Perry E. Van Over

[57] ABSTRACT

A lockable drainage catheter is disclosed for percutaneous insertion into a patient and drainage of fluid therefrom. The drainage catheter includes a flexible tube that is preformed for retaining the distal end of the catheter in the patient. For insertion, the distal end is straightened with the use of a stiffening cannula that is inserted through the hollow passageway of the catheter. When the catheter is inserted in the patient, the stiffening cannula is removed, and a thin cable positioned within the passageway of the catheter is drawn to position the end of the flexible tube to a desired retention configuration. A twisting lock device positioned at the proximal end of the catheter draws the cable through the passageway of the elongated member tube to position the end of the flexible tube to a retention configuration. By twisting the proximal member relative to the distal member of the twisting lock device, the cable wraps around a reel within the device. When the device is twisted to the locked position, a rubber O-ring is compressed resulting in a fluid tight connection. The compressed O-ring provides enough friction to maintain the device in the locked position. A Luer lock connector is affixed to the proximal end of the twisting lock device for connection to a drainage collection system.

11 Claims, 2 Drawing Sheets

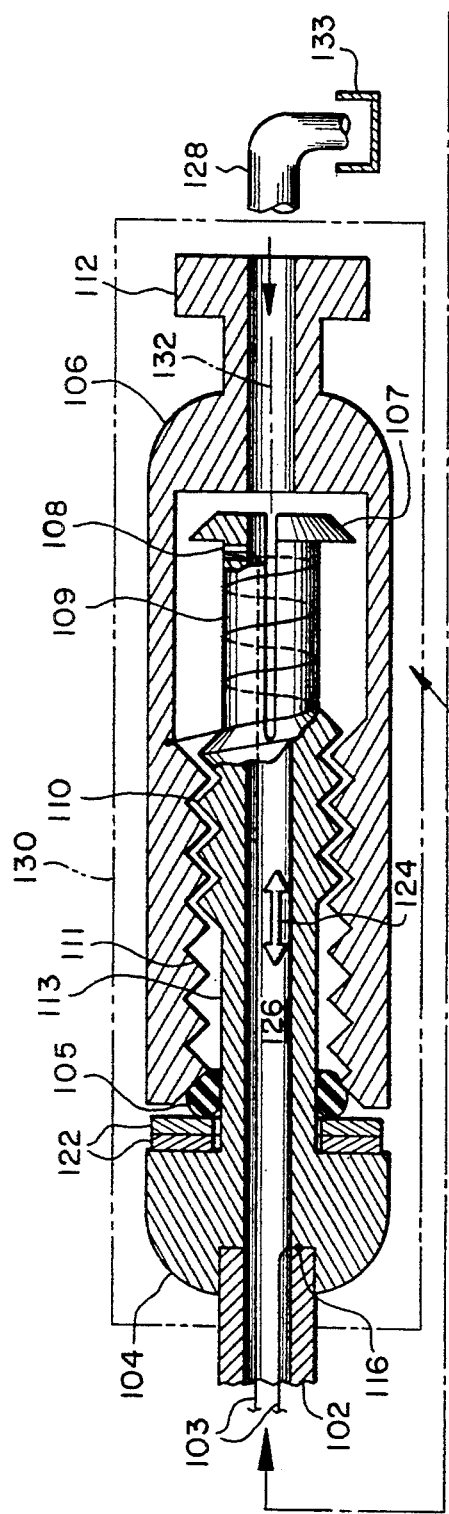
FIG. 2
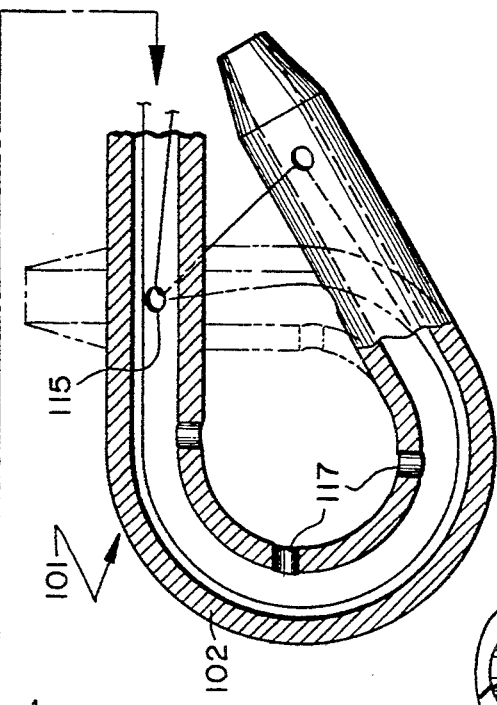
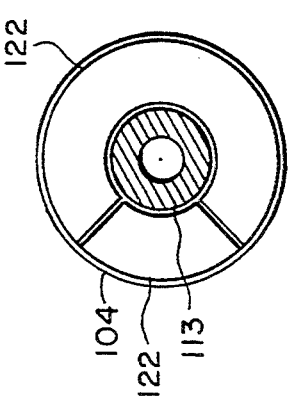
FIG. 3
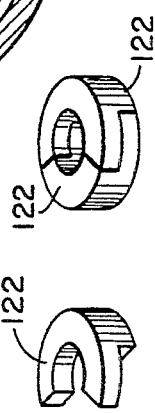
FIG. 4a  FIG. 4b  FIG. 4c

PERCUTANEOUS TWISTING LOCK CATHETER

BACKGROUND OF THE INVENTION

1. Technical Field

This invention relates to catheters and particularly to a catheter having a twisting lock for drawing the distal end into a predetermined configuration.

2. Description Of Related Art

Suprapubic catheterization of the bladder is used to drain the bladder after surgery or when the genitourinary system is plugged by an obstruction. Other pecutaneously inserted catheters are also used to drain the kidney or biliary system as well as to drain abscesses, other sites of fluid collection and other viscera. Still other pecutaneously inserted catheters are gastrostomy feeding tubes.

These catheters are introduced into the patient by means of a large hypodermic needle or trocar which typically pierces the abdominal wall. A wire guide is inserted through the needle, which is then removed. The catheter tube with a stiffening cannula positioned therein is then passed over the wire guide into the cavity. The cannula and wire guide are withdrawn, leaving the catheter in the desired cavity. With respect to the bladder, the advantage of this technique is that irrigation and infection of the urinary tract is minimized. However, one problem with these catheters is that the catheter can be easily pulled out by movement of the body or by the emptying of, for example, the bladder. Another problem is that side ports at the distal end of the catheter may be inadvertently drawn into the abdominal cavity creating potential for severe infections.

Various catheters have been developed with so-called pigtail loops at their distal ends which both ensures drainage of the cavity and prevents accidental removal therefrom. The pigtail loop is tightened by pulling on the proximal end of a flexible tension member which extends through the catheter. With some catheters, the proximal end of the tension member is held in place by axially placing a hollow cap into or over the proximal end of the catheter tube, thus trapping the flexible tension member of which the protruding end may then be cut.

With other catheters, the flexible tension member is trapped between two or more hollow tubes, one of which is slidably inserted axially into the other. A short length of the flexible member is generally left hanging from the catheter tube so that if the tension member becomes loose, it may be retightened.

In a second generation of this flexible member catheter, an external sleeve is slid over the flexible member protruding from the side of the catheter tube of which the flexible member is then wound around and tied about the sleeve.

Although well suited for its intended purpose, the physician is required to grasp and pull on the flexible tension member and to either secure or tie it about the proximal end of the catheter. Such a flexible tension member left exposed at the proximal end allows the patient to untie the member. As a result, the assistance of hospital personnel is required to retie the member. Furthermore, when the flexible tension member is inadvertently released, the retaining loop at the distal end is released with the possibility of the catheter being withdrawn from the patient.

In another catheter developed by the present inventor and described in U.S. Pat. No. 5,041,085, which is specifically incorporated by reference herein, a sleeve device is utilized to secure the lockable flexible tension member and obtain a fluid tight interconnection. This has the disadvantage of not being adjustable, not allowing for partial locked positions.

SUMMARY OF THE INVENTION

To overcome the problems of today's catheters, it is an object of the invention to curl the tip of a catheter tube by using a reel to draw in a thin flexible tension member that pulls the tip of the catheter tube into position.

Another object is to perform the reeling function by way of a longitudinal twisting action, i.e., rotating a portion of the catheter body in a direction generally about a longitudinal centerline of the catheter.

Another object is uniformly wrap the flexible tension member both longitudinally and axially around the reel as it rotates.

Another object is to contain the flexible tension member entirely within the catheter body once it's locked into position.

Another object is to use a reel to both tighten and lock the flexible tension member.

Another object is to have the flexible tension member slide over the reel as it's rotated.

Another object is to have the body fluids conveyed through the center of the reel.

Another object is to tighten the flexible tension member, lock the flexible tension member, and seal the catheter with the same twisting motion.

Another object is to provide a reel with selectable lock positions.

These and other objects of the invention are provided by a catheter for conveying fluid between a human body and a reservoir. The catheter includes a reel for tightening a flexible tension member. The reel has a center hole for conveying the fluid therethrough.

BRIEF DESCRIPTION OF THE DRAWINGS

FIG. 2 depicts the catheter of FIG. 1 in the locked configuration.

FIG. 3 is a cross-sectional view of FIG. 1.

FIG. 4 is a perspective view illustrating the assembly of a pair of spacers.

DESCRIPTION OF THE PREFERRED EMBODIMENT

Figure 1:
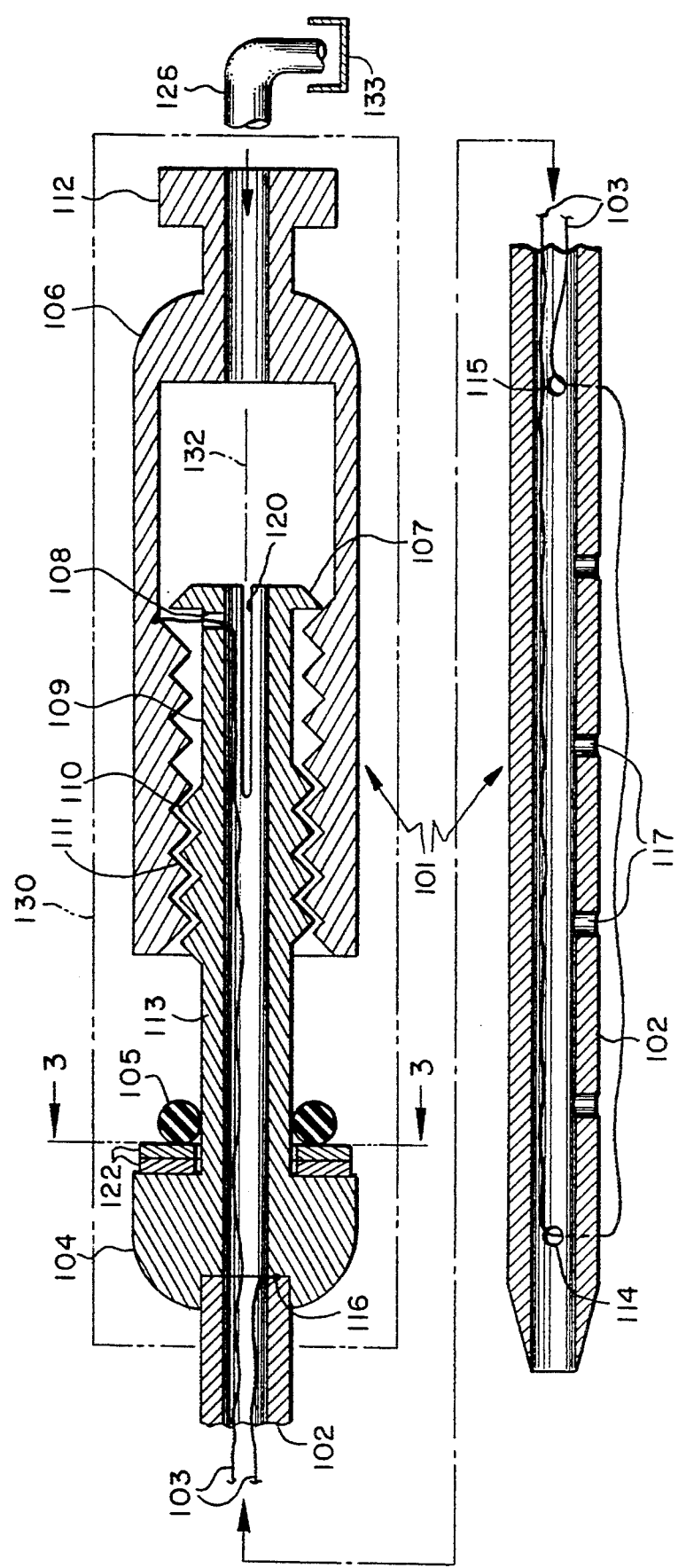
FIG. 1 depicts the percutaneous twisting lock catheter of the present invention in the unlocked configuration.

Depicted in FIG. 1 is a sectioned view of an illustrative percutaneous twisting lock catheter 101 in a relaxed and unlocked configuration prior to percutaneous insertion into a body cavity.

Depicted in FIG. 2 is the same catheter in a locked configuration at a first predetermined limit.

Catheter 101 depicted in FIG. 1 is intended to be used with an inner stiffening cannula over a guide wire (not shown). Before placement of the catheter 101, a thin-wall needle with a stylet inserted therein (now shown) is percutaneously inserted into a body cavity using standard techniques. The stylet is removed and proper placement of the needle is confirmed. A guide wire is then placed into the body cavity and the needle is removed leaving the guide wire in place. Serial dialators are then commonly used to dilate the puncture tract to allow final placement of the catheter 101 with the inner stiffening cannula into the body cavity requiring drainage. The inner stiffening cannula is then removed and the catheter 101 is then formed into the locked configuration depicted in FIG. 2.

As shown in FIGS. 1 and 2, catheter 101 included a flexible tube 102, a flexible tension member 103 (such as a nylon thread or cable) and a catheter body 130 consisting of a distal member 104, an O-ring 105 and a proximal member 106. The distal member 104 consists of a flared end 107 to prevent the device from being unscrewed completely after manufacture. Slots 120 allows flared end 107 to snap into position. A side hole 108 is present in reel 109 of the distal member 104. The side hole 108 is for the flexible tension member 103 to pass through so that it can be anchored to the proximal member 106. The reel 109 of the distal member 104 is where the flexible tension member 103 is wound around the distal member 104 when the proximal member 106 is tightened against O-ring 105 as shown in FIG. 2 in the locked configuration. There is a threaded portion 110 of the distal member 104 around which is the threaded portion 111 of the proximal member 106. By twisting the proximal member 106 and the distal member 104 the proper direction, the threaded portions 110 and 111 will put the proximal and distal members 106 and 105 together against O-ring 105 when spacers 122 are entirely removed from catheter 101. This serves as a mechanical stop limiting the rotation of reel 109 to a first predetermined limit regardless of the tension of item 103. After a preset number of turns around longitudinal centerline 132, the proximal member 106 will compress O-ring 105 against the distal member 104 resulting in a watertight seal. This preset number of turns also results in the flexible tension member 103 being wound around reel 109 of the distal member 104 the same number of turns and results in the flexible tension member 103 being pulled the proper distance to result in complete looping of the tip of flexible tube 102 as indicated by phantom lines in FIG. 2.

The proximal member 106 at the proximal end has a Luer lock connector 112 to allow the catheter 101 to be attached to a reservoir tube 128 so that fluid from the body cavity may drain by gravity or suction into a reservoir 133. The components of catheter 101 generally situated between flexible tube 102 and tubing 128 is referred to as a catheter body 130. Reel 109 includes a hole 126 through which fluid may pass generally parallel to longitudinal centerline 132 in either direction as depicted by arrow 124.

There is a second tubular portion 113 of the distal member 104 which O-ring 105 surrounds. O-ring 105 may be moved toward the proximal member 106 along this second tubular portion 113 of the distal member 104. This would allow space to snap on spacers 122 of various thickness around the second tubular portion 113 of the distal member 104 (see FIGS. 3 and 4). This would allow for a partially closed configuration as indicated by solid lines (as opposed to phantom lines) in FIG. 2. Spacers 122 can be of various thickness or eliminated all together. Spacers 122 provide a user selectable means for providing multiple stop positions of reel 109.

The flexible tension member 103 is anchored at one end to the proximal member 106, and passes through the side hole 108 of the tubular portion of the distal member 106, into the lumen of the distal member 106. The flexible tension member 103 continues distally into the lumen of flexible tube 102 to the distal portion of flexible tube 102 where the flexible tension member 103 would then pass out through one of the draw ports 114 and then back in through one of the draw ports 115 back into the lumen of flexible tube 102 back to an anchor site 116 at the junction between flexible tube 102 and the distal member 104 or to an alternate anchor site on the distal member 104. Multiple side holes 117 are present in the distal end of flexible tube 102.

When flexible tube 102 is formed into the locked configuration within a body cavity, the distal loop formed by locking the catheter 101 helps to prevent accidental removal of the catheter 101 from the body cavity. Additional techniques are commonly used to assist in keeping currently used catheters in place such as suturing these catheters to the skin or using commercially available devices to help anchor these catheters. These methods would apply as well to the catheter 101.

No changes are being proposed concerning the various configurations of flexible tube 102 currently in use, therefore no additional description will be given concerning the elongated member.

It is to be understood that the above-described drainage catheter is merely an illustrative embodiment of the principles of this invention and that other apparatus and catheters may be devised by those skilled in the art without departing from the spirit and scope of this invention. In particular, the distal end of the catheter may be preformed into any desired configuration for positioning and retaining the distal end of the catheter in any part of a patient's body. However the illustrative embodiment illustrates a draininage catheter which is easily manipulated by the physician without having to tie the flexible tension member and allows various partially locked configurations. The underlying principle of this device is the twisting motion resulting in flexible tube 102 being drawn into the twisting lock device consisting of the proximal member 106, distal member 104 and O-ring 105. Once in a locked position, the catheter maintaining a closed system for which fluid may be drained from the patient. Furthermore, one end of the flexible tension member may be attached in any one of a number of well-known ways to the distal end of the elongated member and drawable through one or more draw ports for positioning the distal end for the desired position.

Although the invention is described with respect to a preferred embodiment, modifications thereto will be apparent to those skilled in the art. Therefore, the scope of the invention is to be determined by reference to the claims which follow.

I claim:

1. A catheter for conveying a fluid between a human body and a reservoir tube, comprising:
    a flexible tube adapted to connect to said human body;
    a catheter body coupled to said flexible tube and adapted for coupling to said reservoir tube;
    a reel rotatable about a longitudinal centerline and borne by said catheter body, said reel having a hole adapted to convey said fluid therethrough in a direction substantially parallel to said longitudinal centerline; and
    a flexible tension member extending through said flexible tube and wrapped around said reel.

2. The catheter of claim 1, further comprising a mechanical stop limiting the rotation of said reel after a plurality of revolutions thereof.

3. A catheter for conveying a fluid, comprising:

a catheter body having a proximal member and a distal member in fluid communication with each other to convey said fluid through said catheter body;

a flexible tube coupled to said catheter body;

a reel disposed within said catheter body, said reel being rotatable relative to at least one of said proximal member and said distal member;

a flexible tension member coupled to said flexible tube and said reel such that upon relative rotation of said reel, said flexible tension member wraps a plurality of revolutions around said reel to draw said flexible tube into a predetermined configuration; and a mechanical stop limiting the rotation of said reel to a first predetermined limit after said plurality of revolutions, said mechanical stop limiting the rotation of said reel to said first predetermined limit independent of any tension of said flexible tension member.

4. The catheter of claim 3, further comprising a threaded portion on said reel causing an axial movement of said reel relative to at least part of said catheter body upon rotating said reel, thereby wrapping said flexible tension member both circumferentially and axially along said reel.

5. The catheter of claim 4, wherein said axial movement co-acts with said mechanical stop to limit the rotation of said reel.

6. The catheter of claim 3, wherein said proximal member is rotatable relative to said distal member, and said reel is an integral part of said distal member.

7. The catheter of claim 6, wherein one end of said flexible tension member is anchored to said distal member and an opposite end of said flexible tension member is anchored to said proximal member.

8. The catheter of claim 6, further comprising snap-in means for allowing assembly of said distal member and said proximal member, and for inhibiting disassembly thereof.

9. The catheter of claim 3, further comprising a spacer selectively inserted between said distal member and said proximal member to provide a user selectable second predetermined limit.

10. The catheter of claim 3, further comprising an O-ring between said proximal member and said distal member.

11. A catheter for conveying a fluid, comprising:

a proximal member;

a distal member rotatably connected to said proximal member and in fluid communication therewith to convey said fluid between said distal member and said proximal member;

a flexible tube coupled to at least one of said proximal member and said distal member;

a reel integrally part of said distal member;

a threaded portion on said reel causing an axial movement of said distal member relative to said proximal member upon relative rotation of said reel to said proximal member;

a flexible tension member coupled to said flexible tube and said reel such that upon rotating said distal member relative to said proximal member, said flexible tension member wraps both circumferentially and axially along said reel to draw said flexible tube into a predetermined configuration; and a mechanical stop limiting said axial movement of said distal member relative to said proximal member, thereby limiting the rotation of said reel to a first predetermined limit.

* * * * *